United States Patent
Jung et al.

(10) Patent No.: US 9,580,681 B2
(45) Date of Patent: *Feb. 28, 2017

(54) METHOD OF MANUFACTURING PATTERNED SUBSTRATE FOR CULTURING CELLS, PATTERNED SUBSTRATE, AND PATTERNED CELL CHIP

(71) Applicant: Sungkyunkwan University Foundation for Corporate Collaboration, Gyeonggi-do (KR)

(72) Inventors: Dong Geun Jung, Seoul (KR); Chang Rok Choi, Gyeonggi-do (KR); Kyung Seop Kim, Incheon (KR)

(73) Assignee: Sungkyunkwan University Foundation for Corporate Collaboration, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,190

(22) Filed: Feb. 27, 2015

(65) Prior Publication Data

US 2015/0232806 A1 Aug. 20, 2015

Related U.S. Application Data

(63) Continuation-in-part of application No. 12/872,903, filed on Aug. 31, 2010, now abandoned.

(30) Foreign Application Priority Data

Sep. 1, 2009 (KR) ........................ 10-2009-0082152

(51) Int. Cl.
*C08F 2/46* (2006.01)
*C12N 5/00* (2006.01)
(Continued)

(52) U.S. Cl.
CPC ............... *C12N 5/0068* (2013.01); *B05D 1/32* (2013.01); *B05D 1/62* (2013.01); *C12N 2533/30* (2013.01);
(Continued)

(58) Field of Classification Search
CPC ..... C12N 5/0068; C12N 2535/10; B05D 1/62; B05D 1/32; C08F 2/46
See application file for complete search history.

(56) References Cited

U.S. PATENT DOCUMENTS 7,038,150 B1 * 5/2006 Polosky ............... H01H 1/0036
200/61.45 M
2003/0059537 A1 * 3/2003 Chilkoti ................. B05D 1/283
427/256

(Continued)

FOREIGN PATENT DOCUMENTS

| JP | 2005-521550 A | 7/2005 |
| KR | 10-044880 B | 1/1989 |
| WO | WO-2008/105624 | 9/2008 |

OTHER PUBLICATIONS

Rhee, Seog Woo, et al., "Patterned cell culture inside microfluidic devices". Lab Chip, 2005, 5, 102-107.*
(Continued)

*Primary Examiner* — Bret Chen
(74) *Attorney, Agent, or Firm* — Cesari and McKenna LLP

(57) ABSTRACT

A method of manufacturing a patterned substrate for culturing cells. The method includes the steps of: (1) preparing a substrate, (2) forming a first plasma polymer layer by integrating a first precursor material on the substrate using a plasma, wherein the first plasma layer inhibits cell adsorption, and wherein the first precursor material is a siloxane-based compound having a siloxane functional group with the Si—O—Si linkage, (3) placing a shadow mask having a
(Continued)

Method of manufacturing patterned substrate for cell fixation predetermined pattern on the first plasma polymer layer thus formed, and (4) forming a second patterned plasma polymer layer by integrating a second precursor material using a plasma, wherein the second patterned plasma layer permits culturing of cells, whereby the patterned substrate is obtained.

16 Claims, 8 Drawing Sheets

(51) Int. Cl.
  *B05D 1/00* (2006.01)
  *B05D 1/32* (2006.01)
(52) U.S. Cl.
  CPC ....... *C12N 2535/10* (2013.01); *C12N 2537/00* (2013.01); *C12N 2539/00* (2013.01)

(56) References Cited

U.S. PATENT DOCUMENTS

| | | | |
|---|---|---|---|
| 2005/0089803 A1 | 4/2005 | Bouaidat et al. | |
| 2005/0244961 A1* | 11/2005 | Short | C12N 5/0068 435/366 |
| 2007/0065582 A1* | 3/2007 | Haack | C03C 23/0075 427/255.18 |
| 2007/0122901 A1* | 5/2007 | Morita | A61L 27/38 435/325 |
| 2007/0166815 A1* | 7/2007 | Jung | C07K 1/1077 435/287.2 |
| 2008/0220520 A1* | 9/2008 | Palecek | A01N 1/02 435/374 |
| 2009/0042736 A1 | 2/2009 | Bomer et al. | |
| 2014/0255968 A1* | 9/2014 | Jung | C12N 5/0068 435/29 |
| 2014/0330392 A1* | 11/2014 | Schwartz | A61L 27/306 623/23.74 |
| 2015/0024493 A1* | 1/2015 | Venkatraman | A61L 27/18 435/396 |

OTHER PUBLICATIONS

Saha, Krishanu, et al., "Surface-engineered substrates for improved human pluripotent stem cell culture under fully defined conditions". PNAS, vol. 108, No. 46, Nov. 5, 2011, pp. 18714-18719.*

Tan, John L., et al., "Simple Approach to Micropattern Cells on Common Culture Substrates by Tuning Substrate Wettability". Tissue Engineering, vol. 10, No. 5/6, 2004, pp. 865-872.*

Chen, et al., "Using self-assembled monolayers to pattern ECM proteins and cells on substrates", Methods in Molecular Biology, vol. 139, pp. 209-219.

Cheng, et al., "Plasma-assisted surface chemical patterning for single-cell culture", Biomaterials, vol. 30, pp. 4203-4210, 2009.

Choi, et al., "Selective adhesion of intestinal epithelial cells on patterned films with amine functionalities formed by plasma enhanced chemical vapor deposition", Applied Surface Science, p. 257, p. 398-403.

Curtis, et al., "Reaction of cells to topography", J. Biomater Sci Polymer Ed., vol. 9(12):1313-1329, 1998.

Fuard, et al., "Optimization of poly-di-methylsiloxane (PDMS) substrates for studying cellular adhesion and motility", Microelectronic Engineering, vol. 85(5-6), pp. 1289-1293.

Mann, et al., "Modification of surfaces with cell adhesion peptides alters extracellular matrix deposition" Biomaterials, vol. 20 (23-24):2281-6, 1999.

Selvarash, et al., "A high aspect ratio, flexible, transparent and low-cost Parylene-C-Shadow mask technology for micropatterning applications", Transduvers and Eurosensors, vol. 2, pp. 533-536, 2007.

Uchimura, et al., "On-chip transfection of PC12 cells based on the rational understanding of the role of ECM molecules: efficient, non-viral transfection of PC12 cells using collagen IV", Neuroscience Letters 378 (2005) 40-43.

* cited by examiner

Method of manufacturing patterned substrate for cell fixation

Method of manufacturing patterned substrate for cell fixation after 2 hrs after 8 hrs after 24 hrs (a)                  (b)

METHOD OF MANUFACTURING PATTERNED SUBSTRATE FOR CULTURING CELLS, PATTERNED SUBSTRATE, AND PATTERNED CELL CHIP

CROSS-REFERENCE TO RELATED APPLICATIONS

The present application is a continuation-in-part of and claims priority to U.S. patent application Ser. No. 12/872,903, now abandoned, entitled "Method of Manufacturing Patterned Substrate for Culturing Cells, Patterned Substrate for Culturing Cells, Patterning Method of Culturing Cells, and Patterned Cell Chip," filed in the U.S. Patent and Trademark Office on Aug. 31, 2010 and having a common inventor as the present document.

BACKGROUND OF THE INVENTION

Field of the Invention

The present invention relates to a method of manufacturing a patterned substrate for culturing cells, a patterned substrate for culturing cells, a patterning method for culturing cells, and a cell chip; and more particularly, a method of manufacturing a patterned substrate for culturing cells, a patterned substrate for culturing cells, a patterning method for culturing cells, and a cell chip, in which a substrate capable of inhibiting cell adsorption is manufactured using a plasma and cells are selectively cultured by patterning and integrating many numbers of functional groups on the substrate.

Background Information

Researches relating to human life including a human genome project are rapidly increasing. Information analysis and operation of living organisms are gathering strength with ongoing researches on living organisms. Accordingly, an interest in biochips for rapidly analyzing information of organisms has been dramatically increased more than ever before.

Biochips can be divided by a DNA chip, a protein chip and a cell chip according to a biomaterial which is fixed or cultured on a substrate. In the beginning of the biochip era, a DNA chip appeared as a great issue with understanding of human genetic information but protein chips and cell chips have been recently become new attractions of the biochip with the interest in proteins and cells in which a protein binds. Even though non-specificity binding has been an important problem associated with the protein chip, a variety of notable methods are now being introduced.

Among them, the cell chip which is capable of culturing a large amount of cells without affecting their properties is appeared as the most effective tool to access into various fields including novel drug developments, genomics, and proteomics, etc. The cell chip is different from the protein chip in that the rate of cell growth on a substrate in the cell chip is one of indications representing the performance of the cell chip. Meanwhile, when the growth and division of cells cultured on a substrate is observed, the behavior of the cells will be easily analyzed. For example, an effect of cells to a new drug or response of cells to materials in vivo such as hormones can be easily examined.

Various methods for culturing cells on a substrate have been developed, and can be broadly divided by a method using a biomaterial and a method using physical and chemical characteristics of the substrate itself. In the method using a biomaterial, peptides or proteins are first fixed on a substrate, and cells are cultured using cell receptors contained in their biomaterials [Mann B K, Tsai A T, Scott-Burden T, West J L. Modification of surfaces with cell adhesion peptides alters extracellular matrix deposition. Biomaterials 1999; 20(23-24):2281-6].

Examples of the method using physical and chemical characteristics of a substrate include a method using hydrophobic characteristics, a method using electrical characteristics, a method using surface characteristics [Curtis A S, Wilkinson C D. Reactions of cells to topography. J Biomater SciPolym Ed 1998; 9(12):1313-0.29], a method using collagen [On-chip transfection of PC12 cells based on the rational understanding of the role of ECM molecules: efficient, non-viral transfection of PC12 cells using collagen IV, Neuroscience Letters 378 (2005) 40-43], etc.

There are several drawbacks associated with cell chips of which the most general one is that cells are not cultured well on a substrate. When cells are cultured evenly without conglomeration on a substrate, the cells can grow or divide on the substrate. On the other hand, when cells are not cultured properly on the substrate, the cells fail to grow and divide. Further, successful cell culture means that a small amount of cells are exactly cultured. A small amount of cells has to be exactly cultured on a substrate, which can eventually increase the sensitivity of cell chip.

Second, when cells are cultured on the substrate, their intrinsic properties or organization have to be well maintained. If the cells fail to grow or the cells' characteristics are lost due to the substrate even though the cells are well cultured on the substrate, the cell chip cannot perform its function fully. Therefore, it is required to consider the above factors in the development of cell chips.

To solve the above problems, there is a method of efficiently and effectively performing cell culture using a plasma, which is disclosed in PCT/KR2008/001117. This application discloses a method of manufacturing a substrate for fixing cells, a substrate for fixing cells, a method of fixing cells and a cell chip. This application mentions a method of a substrate for fixing cells, a substrate for fixing cells, a method of fixing cells and a cell chip, which is able to fix cells efficiently by integrating many numbers of functional groups on a substrate using a plasma. However, this application mentions only the method of fixing cells on a substrate using a plasma or the like, but does not mention a method of selectively culturing cells by cell adsorption and inhibition of cell adsorption.

When the substrate is patterned to have a surface for inhibition of cell adsorption and a surface for effective cell culture, it can be applicable in the development of implantable chips and artificial organs, genetic experiment, and drug test. However, the application discloses only the method of uniformly culturing cells, and thus it is impossible to selectively culture a small amount of cells in a desired position.

Therefore, the present inventors have studied and invented a method of manufacturing a patterned substrate for culturing cells, which is capable of selectively culturing cells in the desired position of the substrate using a plasma.

SUMMARY OF THE INVENTION

To solve the above described problems, it is an object of the present invention to provide a method of manufacturing a patterned substrate for culturing cells, which is capable of selectively patterning the surface for effective cell culture on the surface inhibiting cell adsorption.

It is another object of the present invention to provide a patterned substrate for culturing cells, which is manufactured by the above method of manufacturing a patterned substrate for culturing cells.

It is still another object of the present invention to provide a patterning method for culturing cells, which is capable of selectively culturing a small amount of cells in the desired position using the patterned substrate for culturing cells.

It is still another object of the present invention to provide a cell chip manufactured by the patterning method for culturing cells, which is applicable in the development of artificial organs, implantable chips, and novel drugs, genomics, and proteomics.

Advantageous Effects

According to the present invention, a surface capable of inhibiting cell adsorption and a surface capable of effectively culturing cells can be selectively patterned on a substrate.

Further, according to the present invention, cells can be selectively cultured only in a predetermined area by the above patterning method, and their intrinsic properties can be also maintained.

Further, according to the present invention, a small amount of cells can be selectively cultured in a desired position, and thus a cell chip can be mass-produced, leading to cost reduction in manufacture and production.

Further, according to the present invention, the cell chip is applicable in the development of artificial organs, implantable chips, and novel drugs, genomics, and proteomics.

Further, according to the present invention, a large volume of cells can be cultured using a small amount of cells, and thus rapid experiments relating to various cells can be achieved, and it may be suitable for diagnoses of various diseases and profile construction for disorders in special groups.

Further, according to the present invention, the substrate allows uniform fixation of functional groups on a broad surface of the substrate within a short period of time, so that it is possible not only for mass production but also for commercialization.

BRIEF DESCRIPTION OF THE DRAWINGS

The invention description below refers to the accompanying drawings, of which.

Figure 4:
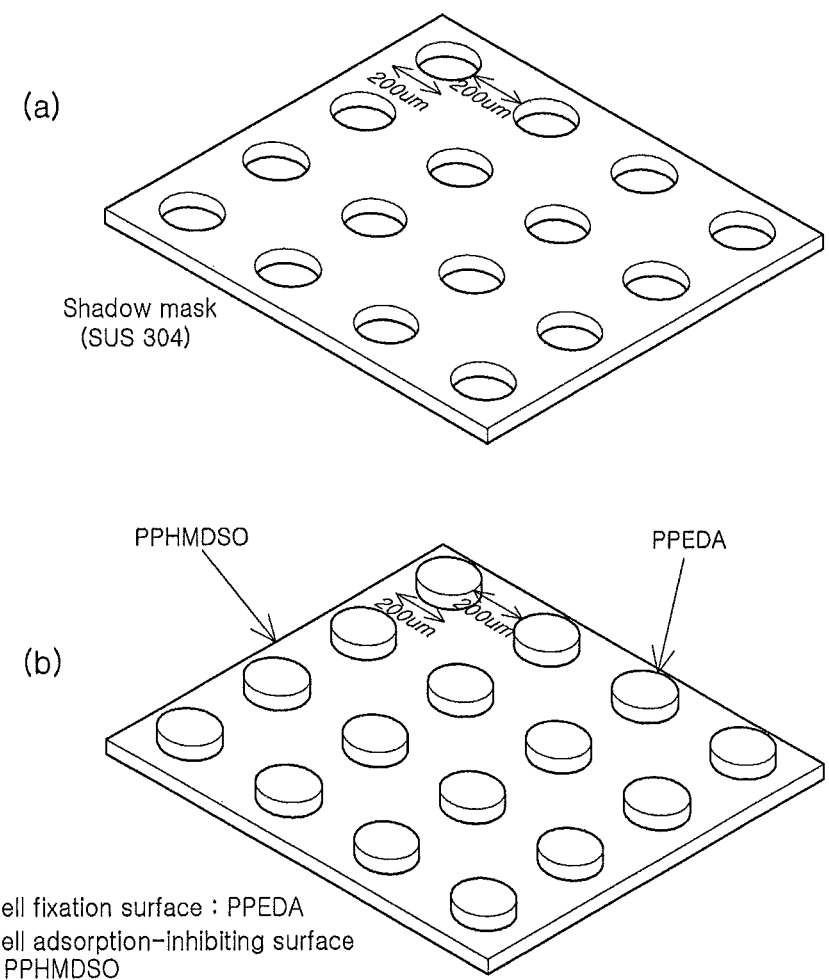
Figure 5:
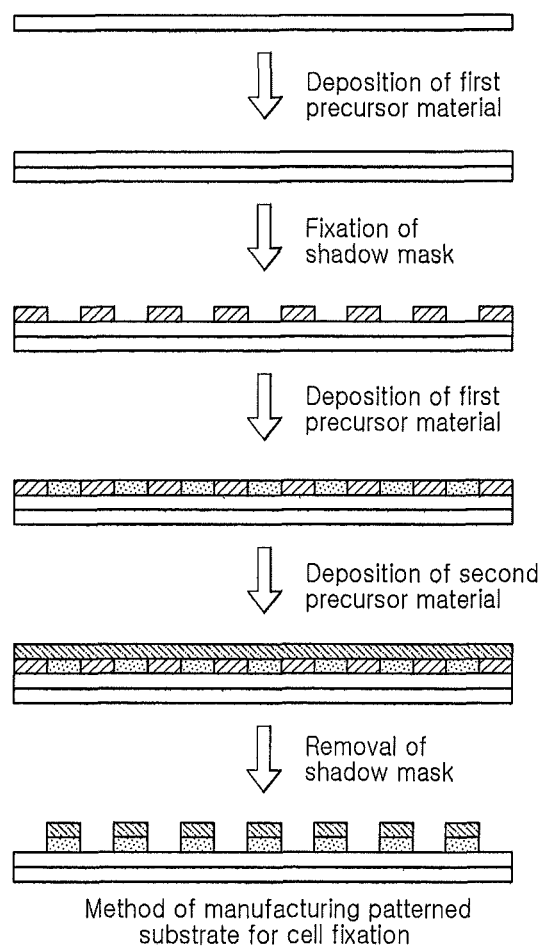
Figure 6:
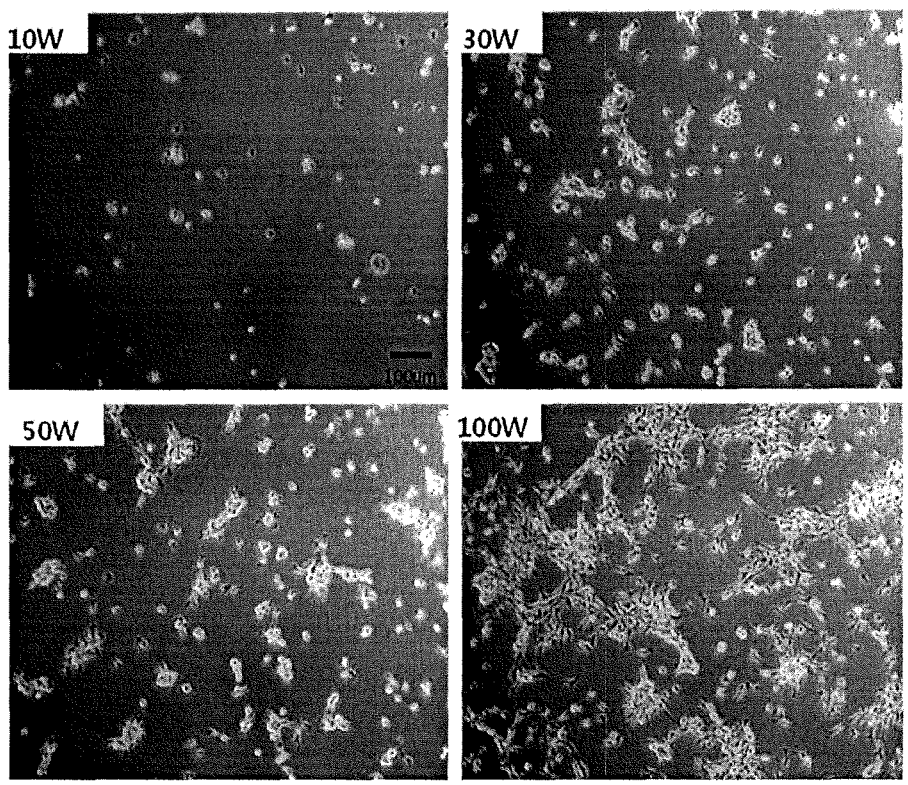
Figure 7:
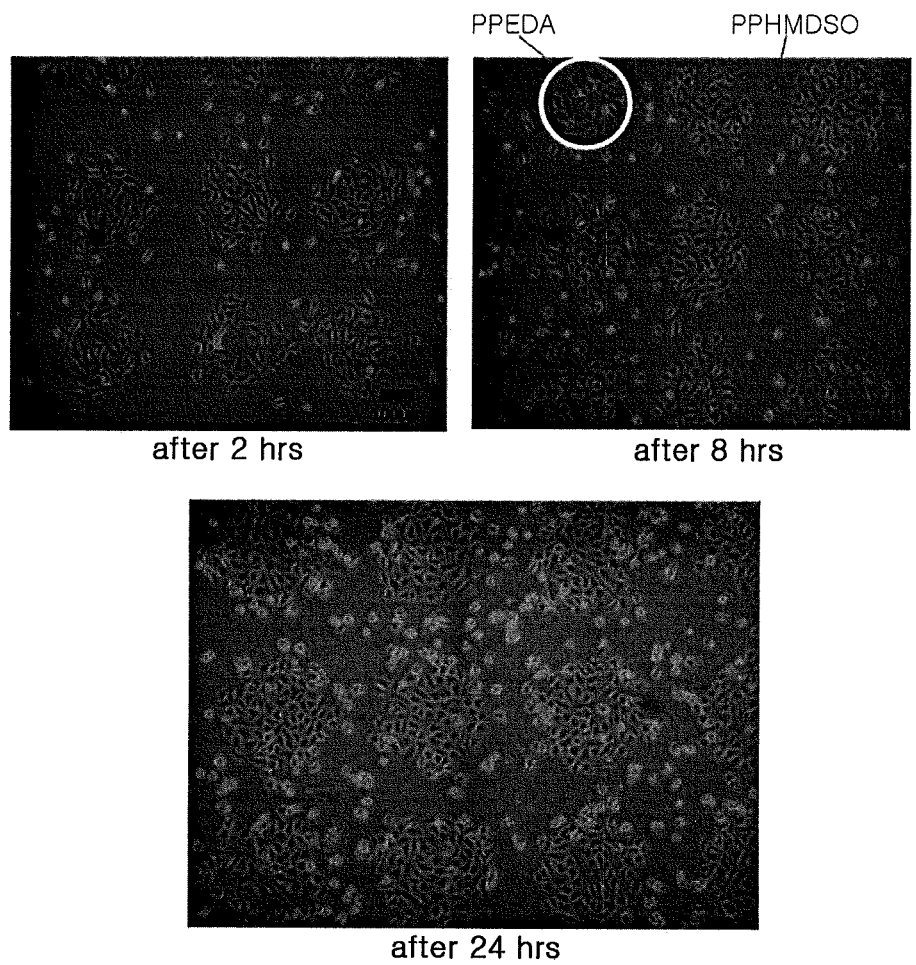

(a) of FIG. 4 is a schematic view of a shadow mask having a predetermined pattern, and (b) of FIG. 4 is a plane view of the patterned substrate for culturing cells according to the present invention;

FIG. 5 is a schematic diagram showing another method of manufacturing a patterned substrate for culturing cells according to the present invention;

FIG. 6 shows photographs of rat intestinal epithelial cells, which were cultured for 24 hrs on the substrates having a plasma polymerized hexamethyldisiloxane thin film as a first plasma polymer layer manufactured by various methods in Preparation Examples 1 to 4; and FIG. 7 shows photographs of rat intestinal epithelial cells, which were cultured for 2 hrs, 8 hrs, and 24 hrs on the patterned substrate for culturing cells according to the present invention.

Figure 8:
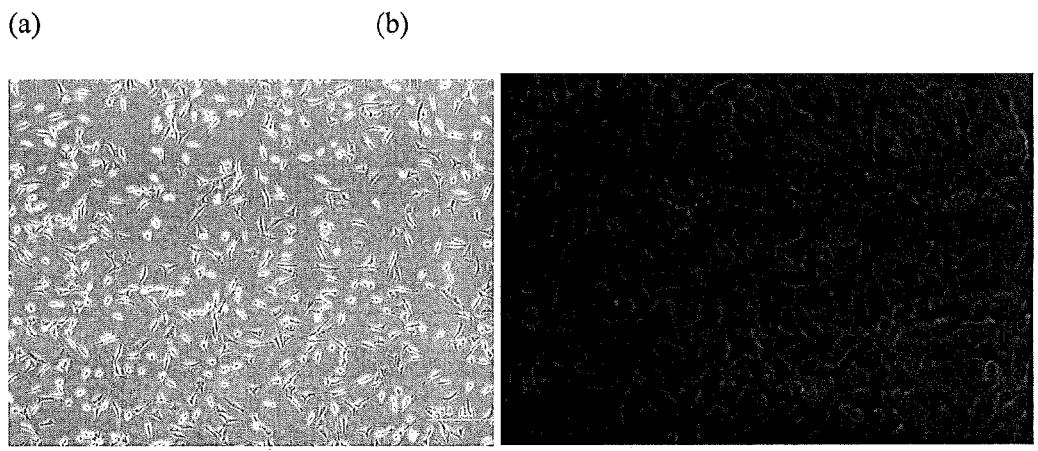
Figure 9:

FIG. 8 shows photographs of NIH 3T3 cells (a) and bovine aortic endothelial cells (b), that were cultured for 24 hrs on the substrate having a plasma polymerized cyclohexane thin film as a first plasma polymer layer manufactured in Preparation Example 5, respectively FIG. 9 shows photographs of NIH 3T3 cells, which were cultured for 24 hrs on the substrate having a plasma polymerized tetrakis(trimethylsilyloxy)silane thin film as a first plasma polymer layer manufactured in Preparation Example 6.

DETAILED DESCRIPTION

Best Mode of the Invention

To achieve the above objects, an aspect of the present invention provides a method of manufacturing a patterned substrate for culturing cells, comprising the steps of: (1) preparing a substrate; (2) forming a first plasma polymer layer by integrating a first precursor material using a plasma on the substrate; (3) placing a shadow mask having a predetermined pattern on the first plasma polymer layer; and (4) forming a second patterned plasma polymer layer by integrating a second precursor material using a plasma.

Figure 3:
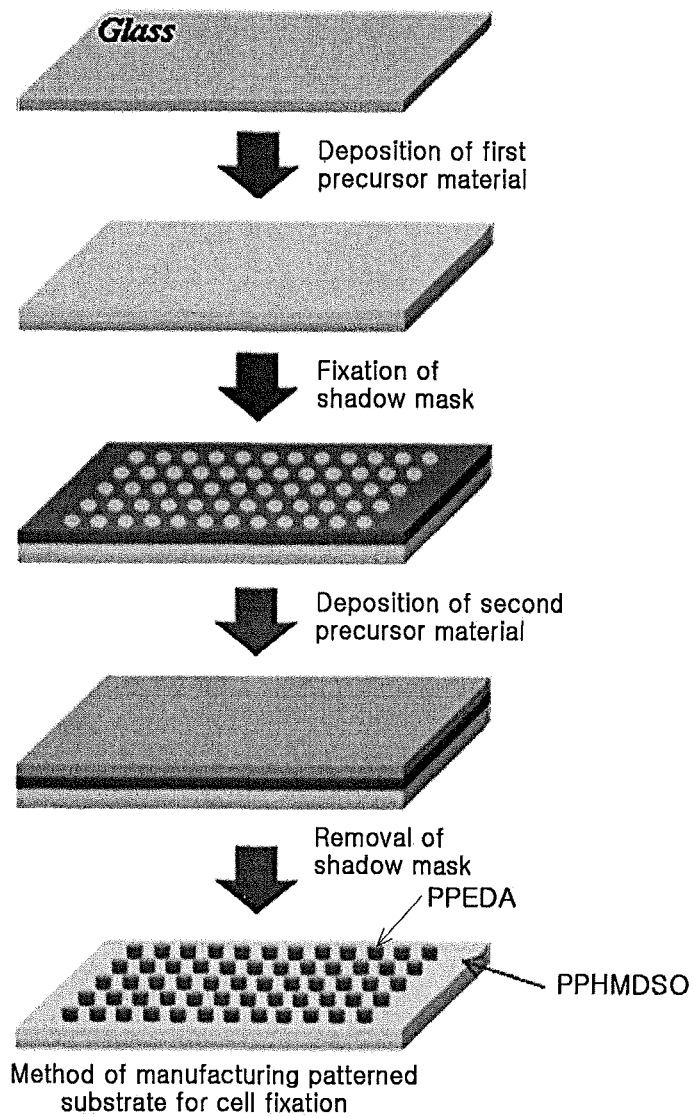
FIG. 3 is a schematic diagram showing the method of manufacturing a patterned substrate for culturing cells according to the present invention.

FIG. 3 is a schematic diagram showing the method of manufacturing a patterned substrate for culturing cells according to the present invention. With reference to FIG. 3, the above steps will be described in detail.

(1) Preparation of Substrate

As used herein, the term "substrate" means all types of plates, on which a precursor material can be integrated using a plasma and in particular, may be selected from the group consisting of glass, plastic, metal and silicone. However, the type of substrate is not particularly limited, as long as the precursor material can be integrated thereon using a plasma. Preferably, a glass slide is prepared as a substrate.

(2) Formation of First Plasma Polymer Layer by Integration of First Precursor Material on Substrate Using Plasma As used herein, the term "plasma" refers to an electrically neutral gas, into which electric energy or heat energy is provided to allow electrons and ions to coexist. Technologies using the plasma have been greatly developed and its uses is more and more active in various fields including plasma etching and plasma enhanced chemical vapor deposition (PECVD) in the semiconductor manufacturing process, the surface treatment of metals or polymers, synthesis of new materials such as synthetic diamond, plasma display panel (PDP) and environmental technologies As used herein, the term "precursor material" means a preceding material capable of forming a plasma polymer layer using a plasma.

The first precursor material of the present invention is not particularly limited, as long as it is able to inhibit cell adsorption. The first precursor material suitable for the present invention can include siloxane-based compounds that are characterized by having a siloxane functional group with the Si—O—Si linkage. It has been considered that the siloxane functional group of the first precursor material plays an important role in preventing cells from adsorbing to a substrate. The siloxane-based compounds as a first precursor material may include linear siloxanes and cyclic siloxanes. Representative examples of the linear siloxane compounds may include hexamethyldisiloxane, octamethyltrisiloxane, decamethyltetrasiloxane, dodecamethylpentasiloxane, and tetradecamethylhexasiloxane, but are not limited thereto. Representative examples of the cyclic siloxane compounds may include hexamethylcyclotrisiloxane, octamethylcyclotetrasiloxane, decamethylcyclopentasiloxane, and dodecamethylcyclohexasiloxane, but are not limited thereto. Non-siloxane-based compounds such as styrene may be used as a first precursor material in the preparation of a first plasma polymer layer according to the present invention.

Preferably, the first precursor material can be a siloxane-based compound represented by the following formula 1:

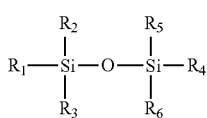

[Formula 1]

wherein R1, R2, and R3 are independently hydrogen or C1-C4 alkyl, and R4, R5, and R6 are independently hydrogen, C1-C4 alkyl or trialkylsilyloxy.

More preferably, the first precursor material suitable for the present invention is hexamethyldisiloxane represented by the following Formula 2, octamethyltrisiloxane represented by the following Formula 3, and tetrakis(trimethylsilyloxy)silane represented by the following Formula 4:

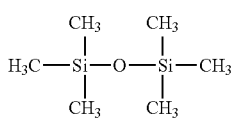

[Formula 2]

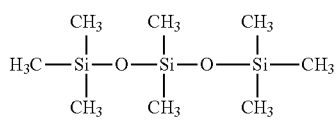

[Formula 3]

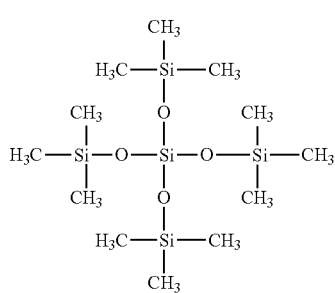

[Formula 4]

Preferably, the first precursor material can be a siloxane-based compound represented by the following formula 5:

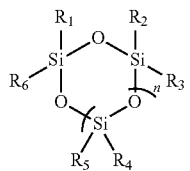

[Formula 5]

wherein R1, R2, R3, R4, R5, and R6 are independently hydrogen or C1-C4 alkyl, and n is an integer ranging from 1 to 3.

The reason is that the plasma polymer layer formed of the above materials inhibits the binding between the substrate and cells, and thus it is excellent in teml of inhibition of cell adsorption.

As used herein, the term "integration" means to degrade the precursor material using a plasma energy and to form a plasma polymer layer by the degraded by-products.

The first plasma polymer layer may be formed by a plasma enhanced chemical vapor deposition method.

Figure 1:
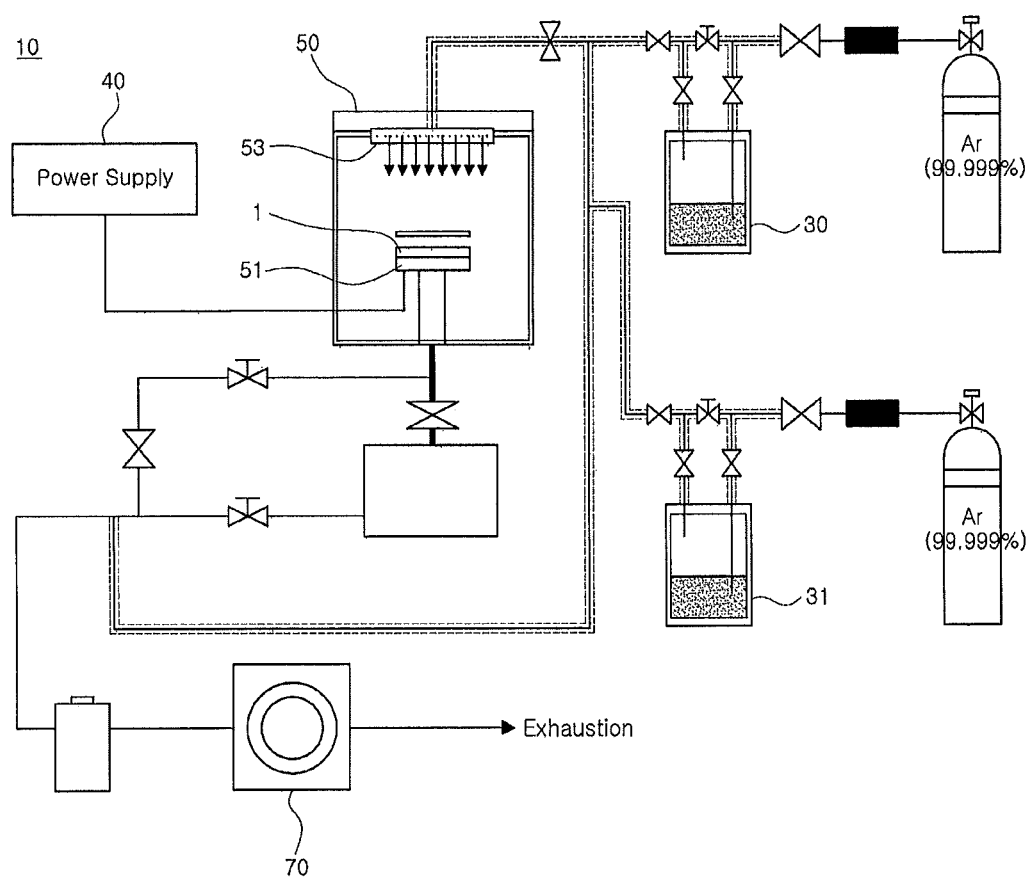
FIG. 1 is a schematic view of plasma enhanced chemical vapor deposition apparatus 10 to form a first plasma polymer layer on a substrate.

The plasma enhanced chemical vapor deposition apparatus used to perform step (2) will be described in detail with reference to FIG. 1. FIG. 1 is a schematic view of plasma enhanced chemical vapor deposition apparatus 10 to form the first plasma polymer layer on a substrate.

With reference to FIG. 1, the constitution of the plasma enhanced chemical vapor deposition apparatus 10 will be described in detail. The apparatus includes a plasma reaction chamber 50 where plasma is formed, a vacuum part including a vacuum pump 70 to control inner pressure of the plasma reaction chamber 50, a gas injection part including a bubbler 30, 31 to inject the first precursor material in the gas state into the plasma reaction chamber 50, and a power supply device 40 to supply a voltage to an internal electrode (SB) or a bottom electrode arranged inside the plasma reaction chamber 50. A substrate holder 51 and the internal electrode (SB) to support the substrate holder 51 by being arranged at the lower part of the substrate holder 51 are sequentially installed inside the plasma reaction chamber 50.

The step of forming a first plasma polymer layer by integrating a first precursor material on the substrate using the plasma enhanced chemical vapor deposition apparatus 10 will be described in detail.

First, a substrate 1 is installed on the substrate holder 51 inside the plasma reaction chamber 50. Subsequently, the pressure inside the plasma reaction chamber 50 is lowered to several mili torr (mtorr), which is closer to the vacuum state, by using the vacuum pump 70, and a first precursor material is then injected along with a carrier gas through the gas injection part into the plasma reaction chamber 50. Here, when a voltage is supplied to the internal electrode (SB) using the power supply device, the plasmas generated by the internal electrode (SB) are formed between the substrate 1 and the outer wall of the plasma reaction chamber 50. At this time, while the first precursor material is polymerized by the generated plasma, the first plasma polymer layer is deposited uniformly on the substrate 1.

In this connection, either the external electrode or the internal electrode may be used, but when the internal electrode is only used, it is more efficient and effective for the deposition of the first plasma polymer layer. In addition, the power of the power supply device of the plasma reaction chamber 50 applied to the internal electrode (SB) is preferably 10 W.

Further, before the first precursor material is injected into the plasma reaction chamber 50, it is preferable to vaporize the first precursor material. The first precursor material may be vaporized by heating it using the bubbler 30, 31 and the vaporization temperature is preferably 50° C. to 116° C. Most preferably, the first precursor material is vaporized at the temperature of 30° C. to 70° C., and plasma-deposited.

The first precursor material may be preferably injected along with a carrier gas into the plasma reaction chamber 50. The carrier gas to be used may be Ar, N2, He or 112, and more preferably Ar. A flow rate of the carrier gas into the plasma reaction chamber 50 is preferably 10 to 50 sccm, and more preferably 15 sccm.

Temperature of the substrate 1 inside the plasma reaction chamber 50 is preferably a room temperature, and pressure inside the plasma reaction chamber 50 may be 10 mtorr to several torr, and preferably 500 mtorr.

In a preferred embodiment, the substrates having a first plasma polymer layer, in which a plasma polymerized hexamethyldisiloxane thin film was deposited on a glass slide by plasma enhanced chemical vapor deposition (PECVD) using hexamethyldisiloxane as a first precursor material, were manufactured (see Preparation Examples 1 to 4). In order to examine inhibitory effects of the substrates on cell adsorption, rat intestinal epithelial cells were cultured thereon for 24 hrs. As a result, it has been found that the rat intestinal epithelial cells cannot adsorb to the substrates on which a plasma polymerized hexamethyldisiloxane thin film as a first plasma polymer layer was formed (see Experimental Example 1, FIG. 6).

In another embodiment, in order to investigate whether such an inhibitory effect on cell adsorption are specific to the siloxane-based compound such as hexamethyldisiloxane, an inhibitory effect of cyclohexane, which has been conventionally used as a precursor in the preparation of a thin film on a substrate, was compared therewith. The substrate having a first plasma polymer layer, in which a plasma polymerized cyclohexane thin film was deposited on a glass slide by PECVD using cyclohexane as a first precursor material, were manufactured (see Preparation Example 5). NIH 3T3 mouse embryo fibroblast cells and bovine aortic endothelial cells were then cultured on the thus manufactured substrate for 24 hrs. As a result, different from the substrate on which a plasma polymerized hexamethyldisiloxane thin film as a first plasma polymer layer was formed, both of the NIH 3T3 cells and bovine aortic endothelial cells were adsorb on the substrate, where a plasma polymerized cyclohexane thin film was formed, and grown thereon regardless of the types of cell (see Experimental Example 2, FIG. 8). These results suggest that being the precursor materials used for the preparation of a thin film on a substrate do not mean that they exhibit inhibitory effects on cell adsorption, and such an inhibitory effect on cell adsorption is specific to the siloxane-based compound having a siloxane functional group such as hexamethyldisiloxane.

In still another embodiment, in order to examine the inhibitory effect of other siloxane-based compounds besides hexamethyldisiloxane, the substrate having a first plasma polymer layer, in which a plasma polymerized tetrakis(trimethylsilyloxy)silane thin film was deposited on a glass slide by PECVD using tetrakis(trimethylsilyloxy)silane as a first precursor material, were manufactured (see Preparation Example 6). As a result of culturing the NIH 3T3 cells on the thus manufactured substrate, it has been found that the cells cannot adsorb on the substrate where a plasma polymerized tetrakis(trimethylsilyloxy)silane thin film as a first plasma polymer layer was formed thereon (see Experimental Example 3, FIG. 9).

These results have confirmed that the siloxane-based compounds having a siloxane functional group can be effectively used for the preparation of a first plasma polymer layer according to the present invention as a first precursor material.

(3) Placement of Shadow Mask Having Predetermined Pattern on First Plasma Polymer Layer As used herein, the term "shadow mask" means a thin metal plate with tiny holes that allows exposing a desired specific region. The material and shape of the shadow mask are not particularly limited, as long as it is placed on the first plasma polymer layer and forms the second plasma polymer layer in a predetermined pattern in Step (4) as described in below.

(a) of FIG. 4 is a schematic view of a shadow mask having a predetermined pattern. With reference to (a) of FIG. 4, in the shadow mask of the present invention, the predetermined pattern is provided with a plurality of holes having a diameter of 200 μm, and a space between the holes is 200 μm. The material is Stainless Steel 304. However, it is apparent that the material and shape of the shadow mask can be changed by a user.

(4) Formation of Second Plasma Polymer Layer by Integrating Second Precursor Material Using Plasma The second precursor material of the present invention is not particularly limited, as long as it is able to culture cells on the substrate without cell modification. However, the precursor material of the present invention may be any precursor material having various types of function groups, such as an amine group, an aldehyde group, a carboxyl group, and a thiol group, and preferably a precursor material having an amine group. Moreover, the second precursor material may be preferably ethylenediamine, acetonitrile, allylamine propylamine, cycloheptane, cyclohexane, cyclopentane or the like, and most preferably ethylenediamine.

The reason is that the plasma polymer layer formed of the above materials is able to culture cells on the substrate without cell modification, and thus it is excellent in term of improvement of cell culture.

Preferably, the second plasma polymer layer may be formed by inductively coupled plasma enhanced chemical vapor deposition.

Figure 2:
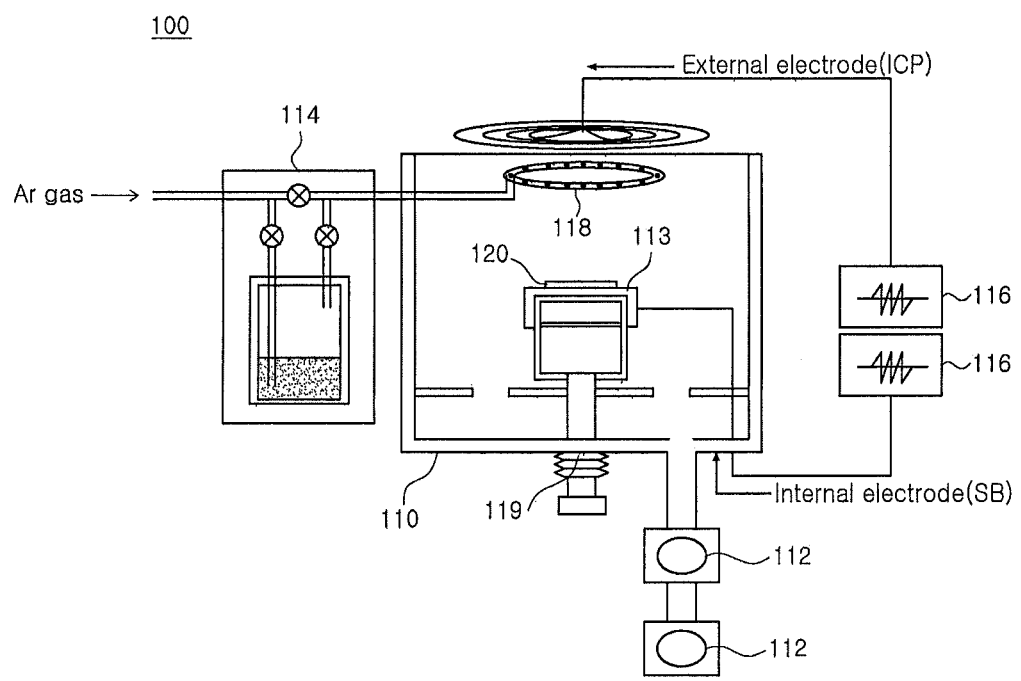
FIG. 2 is a schematic view of inductively coupled plasma enhanced chemical vapor deposition apparatus 100 to manufacture the patterned substrate for culturing cells according to the present invention.

The inductively coupled plasma enhanced chemical vapor deposition apparatus 100 used to perform step (4) will be described in detail with reference to FIG. 2. FIG. 2 is a schematic view of inductively coupled plasma enhanced chemical vapor deposition apparatus 100 to manufacture the patterned substrate for culturing cells according to the present invention.

With reference to FIG. 2, the constitution of the inductively coupled plasma enhanced chemical vapor deposition apparatus 100 will be described in detail. The apparatus includes a reaction chamber 110 where plasma is formed, a vacuum part including a vacuum pump 112 to control inner pressure of the plasma reaction chamber 110, a gas injection part including a bubbler 114 to inject the second precursor material in the gas state into the plasma reaction chamber 110, and a power supply device to supply a voltage to an external electrode (ICP; Inductively Coupled Plasma) arranged on the upper part of the plasma reaction chamber 110 and an internal electrode (SB; Substrate bias) arranged inside the plasma reaction chamber 110. A substrate holder 113 and the internal electrode (SB) to support the substrate holder 113 by being arranged at the lower part of the substrate holder 113 are sequentially installed inside the plasma reaction chamber 110.

Meanwhile, the external electrode (ICP) and the internal electrode (SB) may be any electrode which can be used for general plasma enhanced chemical vapor deposition apparatus, regardless of material and shape. In particular, the shape of the external electrode (ICP) is preferably a flat circular coil, and the material of the internal electrode (SB) is preferably a material which does not have chemical reactions and be environmental friendly, and more preferably a material made of stainless.

The step of forming a second plasma polymer layer using the inductively coupled plasma enhanced chemical vapor deposition apparatus 100 will be described in detail.

A substrate 120, on which the first plasma polymer layer is formed, is installed on the substrate holder 113 inside the plasma reaction chamber 110. The shadow mask having a predetermined pattern is fixed on the substrate 120, on which the first plasma polymer layer is formed. Subsequently, the pressure inside the plasma reaction chamber 110 is lowered to several mili torr (mtorr), which is closer to the vacuum state, by using the vacuum pump 112, and a second precursor material is then injected along with a carrier gas through the gas injection part into the plasma reaction chamber 110. Here, when a voltage is supplied to the external electrode (ICP) and the internal electrode (SB) using the power supply device, the plasmas generated by the external electrode (ICP) and the internal electrode (SB) are formed between the substrate 120 having the first plasma polymer layer and the outer wall of the plasma reaction chamber 110. At this time, while the second precursor material having a functional group is polymerized by the generated plasma, a second plasma polymer layer is deposited selectively on the substrate 120 having the first plasma polymer layer.

In this connection, either the external electrode or the internal electrode may be used. However, when both electrodes are used, it is more efficient and effective for the deposition of the patterned substrate for culturing cells. In addition, the power of the power supply device of the plasma reaction chamber 110 applied to the external electrode (ICP) may be preferably 3 W, 30 W or 70 W, and more preferably 3 W. The power applied to the internal electrode (SB) may be preferably 3 W to 50 W, and more preferably 3 W.

Further, before the second precursor material is injected into the plasma reaction chamber 110, it is preferable to vaporize the second precursor material. The second precursor material may be vaporized by heating it using the bubbler 114 and the vaporization temperature is preferably 50° C. to 116° C. Most preferably, the second precursor material is vaporized at the temperature of 30° C. to 70° C., and plasma-deposited.

Further, the second precursor material may be preferably injected along with a carrier gas into the plasma reaction chamber 110. The carrier gas to be used may be Ar, N2, He or H2, and more preferably Ar. A flow rate of the carrier gas into the plasma reaction chamber 110 is preferably 10 to 50 sccm, and more preferably 15 sccm.

Temperature of the substrate 120 having the first plasma polymer layer inside the plasma reaction chamber 110 is preferably a room temperature, and pressure inside the plasma reaction chamber 110 may be 10 mtorr to several torr, and preferably 30 mtorr.

In the preferred embodiment, the present invention relates to a method of manufacturing a patterned substrate for culturing cells, further comprising the step of forming a first patterned plasma polymer layer by re-integrating the first precursor material using a plasma between steps (3) and (4).

FIG. 5 is a schematic diagram showing another method of manufacturing a patterned substrate for culturing cells according to the present invention. With reference to FIG. 5, the above steps will be described in detail.

The method of manufacturing a patterned substrate for culturing cells described in FIG. 5 is different from the method described in FIG. 3 in that the first precursor material is deposited on the first plasma polymer layer in a patterned shape again, and the second plasma polymer layer is deposited thereon.

This manner can be employed, when the precise patterning is required in the method of manufacturing a patterned substrate for culturing cells. It is because that even though the first plasma polymer layer is formed using the identical first precursor material, adhesion degree of the second plasma polymer layer varies depending on the voltage supply condition.

For example, the second plasma polymer layer is deposited well on the first plasma polymer layer formed by supplying a voltage of 10 W to the internal electrode (SB), compared to the first plasma polymer layer formed by supplying a voltage of 70 W to the internal electrode (SB).

Meanwhile, an increase in SN ratio can be achieved by this manner.

In another embodiment, the present invention relates to a patterned substrate for culturing cells, manufactured by the above described method of manufacturing a patterned substrate for culturing cells.

(b) of FIG. 4 is a plane view of the patterned substrate for culturing cells according to the present invention.

With reference to (b) of FIG. 4, the patterned substrate for culturing cells has convex portions having a diameter of 200 μm, and a space between the convex portions is 200 μm. In this connection, the first plasma polymer layer is formed on the substrate, and the second plasma polymer layer is formed on the first plasma polymer layer in a convex shape. That is, manufactured is a substrate for culturing cells, in which the second plasma polymer layer is patterned in a predetermined shape.

In still another embodiment, the present invention related to a patterning method for culturing cells, comprising the steps of preparing a patterned substrate for culturing cells by the above described method of manufacturing a patterned substrate for culturing cells; and culturing cells on the patterned substrate for culturing cells.

As used herein, the term "cell" refers to the fundamental structural and functional unit of all living organisms, and the cell type is not particularly limited, for example, cells isolated or activated from the liver, kidney, spleen, bone, bone marrow, thymus, heart, muscle, lung, brain, testis, ovary, islet, intestinal, ear, skin, gall bladder, prostate, bladder, embryos, immune system, and hematopoietic system. Preferably, the cell is selected from the group consisting of microorganisms, cells and organs of animal/plant, neural cells, and endothelial cells.

Further, the method of culturing the above described cells on the second plasma polymer layer is not particularly limited, which is a well-known method. Therefore, a description of the method will be omitted.

In still another embodiment, the present invention relates to a cell chip, in which cells are cultured on the patterned substrate for culturing cells manufactured by the above described method of manufacturing a patterned substrate for culturing cells.

As used herein, the term "cell chip" means a biochip capable of detecting multiple physiological signals through cell responses, which cannot be detected by the conventional methods.

Preferably, the cell type is not particularly limited, for example, cells isolated or activated from the liver, kidney, spleen, bone, bone marrow, thymus, heart, muscle, lung, brain, testis, ovary, islet, intestinal, bone marrow, ear, skin, gall bladder, prostate, bladder, embryos, immune system, and hematopoietic system. Preferably, the cell is selected from the group consisting of microorganisms, cells and organs of animal/plant, neural cells, and endothelial cells.

Hereinafter, the preferred Examples are provided for better understanding. However, these Examples are for illustrative purposes only, and the invention is not intended to be limited by these Examples.

MODE FOR THE INVENTION

Preparation Example 1

Formation of First Plasma Polymer Layer on Substrate Using Hexamethyldisiloxane

A plasma polymerized hexamethyldisiloxane (PPH-MDSO) thin film prepared by plasma enhanced chemical vapor deposition using hexamethyldisiloxane as a first precursor material was deposited on a glass slide having a size of 75 mm×25 mm (Corning Microslide Plain, Cat#: 2947, Corning, N.Y.).

Specifically, the deposition was performed using a plasma enhanced chemical vapor deposition apparatus depicted in FIG. 1. The plasma reaction chamber 50 has a cylindrical shape of stainless material. Hexamethyldisiloxane monomer was placed into the bubbler 30, 31 which was heated at 50° C. Hexamethyldisiloxane molecule was vaporized by using an inert gas of argon as a carrier gas and injected into the plasma reaction chamber 50. SB power was supplied to attach the rf generator to a slide substrate holder 51 to generate plasma around the slide. Here, the wall surface of the plasma reaction chamber 50 was put to earth. Meanwhile, the glass slide was washed with ultrasonic waves with trichloroethylene, acetone and methanol in this order, before it was placed in the plasma reaction chamber 50. The pressure of the plasma reaction chamber 50 was adjusted to about several mtorr using the vacuum pump 70. During the deposition, the substrate was maintained at room temperature and a flow rate of argon was maintained at 15 sccm. At this time, the deposition pressure of the plasma reaction chamber 50 was maintained at 500 mtorr, the internal electrode (SB) of the plasma reaction chamber 50 was maintained at 10 W, and the deposition was performed for 5 min. In this manner, a substrate having a first plasma polymer layer, in which a plasma polymerized hexamethyldisiloxane thin film was deposited on a glass slide, was manufactured.

Preparation Example 2

Formation of First Plasma Polymer Layer on Substrate Using Hexamethyldisiloxane

A substrate having a first plasma polymer layer, in which a plasma polymerized hexamethyldisiloxane thin film was deposited on a glass slide, was manufactured in the same manner as in Preparation Example 1, except that the internal electrode (SB) of the plasma reaction chamber 50 was maintained at 30 W in Preparation Example 2.

Preparation Example 3

Formation of First Plasma Polymer Layer on Substrate Using Hexamethyldisiloxane

A substrate having a first plasma polymer layer, in which a plasma polymerized hexamethyldisiloxane thin film was deposited on a glass slide, was manufactured in the same manner as in Preparation Example 1, except that the internal electrode (SB) of the plasma reaction chamber 50 was maintained at 50 W in Preparation Example 3.

Preparation Example 4

Formation of First Plasma Polymer Layer on Substrate Using Hexamethyldisiloxane

A substrate having a first plasma polymer layer, in which a plasma polymerized hexamethyldisiloxane thin film was deposited on a glass slide, was manufactured in the same manner as in Preparation Example 1, except that the internal electrode (SB) of the plasma reaction chamber 50 was maintained at 100 W in Preparation Example 4.

Experimental Example 1

Rat intestinal epithelial cell-18 (IEC-18) was used to perform the experiment in order to examine whether the substrates having a first plasma polymer layer manufactured in Preparation Examples 1, 2, 3 and 4 are able to inhibit cell adsorption.

Rat intestinal epithelial cells were cultured on the substrates having a first plasma polymer layer manufactured in Preparation Examples 1, 2, 3 and 4 so as to examine whether the adsorption of intestinal epithelial cells is inhibited on the substrates. A culture medium was prepared by adding FBS (Fetal Bovine Serum) into DMEM (Dulbecco's modified Eagle's medium) including 4500 mg/l of high glucose to be a concentration of 20%, and supplemented with penicillin/streptomycin and insulin. The external condition while the cells were cultured on the substrate was 37° C., 5% $CO_2$ environment (in a cell incubator).

FIG. 6 shows photographs of rat intestinal epithelial cells, which were cultured for 24 hrs on the substrates having a first plasma polymer layer manufactured in Preparation Examples 1, 2, 3 and 4, and it can be seen that the substrate having a first plasma polymer layer manufactured in Preparation Example 1 shows the most effective inhibitory effect on cell adsorption.

Preparation Example 5

Formation of First Plasma Polymer Layer on Substrate Using Cyclohexane

A plasma polymerized cyclohexane (PPCHex) thin film was deposited on a glass slide (Corning microslide plain, Cat#: 2947, Corning, N.Y.) by using ICP-CVD with cyclohexane (Aldrich Chemical Company) as a precursor. The deposition system used in this example is illustrated schematically in FIG. 1. The deposition chamber made of stainless steel has a cylindrical shape. The diameter and the height of the deposition chamber are 30 cm and 28 cm, respectively. The cyclohexane used as a first precursor material was heated to 50° C. in a bubbler. Inert Ar gas was used to carry vaporized cyclohexane molecules into the deposition chamber. The inductively coupled plasma (ICP) was generated around a shower ring by using a circular coil connected to a 13.56-MHz radio-frequency (r.f.) generator through a matching network. The slide bias (SB) power, which also generates plasma around the slide, was provided by connecting the slide holder to another r.f. generator. The deposition chamber walls were grounded.

Before being loaded into the deposition chamber, the glass slides were cleaned sequentially in trichloroethylene, acetone, and methanol. The base pressure of the deposition chamber was less than ~10-5 Torr when the chamber was pumped with a turbo-molecular pump. PPCHex films were deposited at a slide temperature of ~27° C. and an Ar gas flow rate of 20 sccm. The deposition pressure was kept at 200 mTorr, and the deposition time was maintained at 30 sec. The ICP power was maintained at 15 W, and the SB power was varied from 10 W to 70 W. In this manner, the substrate having a first plasma polymer layer, in which a plasma polymerized cyclohexane thin film was deposited on a glass slide, was manufactured.

Experimental Example 2

In order to examine whether the substrate having a first plasma polymer layer manufactured in Preparation Example 5 is able to inhibit cell adsorption, NIH 3T3 mouse embryo fibroblast cells and bovine aortic endothelial cells were cultured thereon, respectively. A culture medium was prepared by adding FBS (Fetal Bovine Serum) into DMEM (Dulbecco's modified Eagle's medium) including 4500 mg/l of high glucose to be a concentration of 20%, and supplemented with penicillin/streptomycin and insulin. The external condition while the cells were cultured on the substrate was 37° C., 5% CO2 environment (in a cell incubator).

FIG. 8 shows photographs of the NIH 3T3 cells (a) and bovine aortic endothelial cells (b), that were cultured for 24 hrs on the substrate having a first plasma polymer layer manufactured in Preparation Example 5, respectively. As shown in FIG. 8, different from the substrate having a plasma polymerized hexamethyldisiloxane thin film as a first plasma polymer layer, both of the NIH 3T3 cells and bovine aortic endothelial cells were absorbed on the substrate having a plasma polymerized cyclohexane thin film and grown thereon. These results suggest that cyclohexane is not suitable for using a first precursor material according to the present invention to inhibit cell adsorption to a substrate.

Preparation Example 6

Formation of First Plasma Polymer Layer on Substrate by Using Tetrakis(Trimethylsilyloxy)Silane The first plasma polymer film was fabricated by PECVD system using tetrakis(trimethylsilyloxy)silane (TTMSS) as a first precursor material contained in a bubbler. The bubbler containing TTMSS was heated to 90° C., vaporizing the precursor solution. Using the helium (He) gas having ultra-high purity of 99.999% as a carrier gas, the vaporized precursor was sprayed on the Si substrate through a shower head of the reactor for plasma deposition. The deposition was performed at the reactor pressure of 6.6×10-1 Torr, and at room temperature. The plasma power supplied by the radio frequency (RF) generator was changed from 10 to 50 W, and the plasma frequency was 13.56 MHz.

Experimental Example 3

In order to examine whether the substrate having a first plasma polymer layer manufactured in Preparation Example 6 is able to inhibit cell adsorption, NIH 3T3 mouse embryo fibroblast cells were cultured thereon. A culture medium was prepared by adding FBS (Fetal Bovine Serum) into DMEM (Dulbecco's modified Eagle's medium) including 4500 mg/l of high glucose to be a concentration of 20%, and supplemented with penicillin/streptomycin and insulin. The external condition while the cells were cultured on the substrate was 37° C., 5% CO2 environment (in a cell incubator).

FIG. 9 shows photographs of NIH 3T3 cells, which were cultured for 24 hrs on the substrate having a first plasma polymer layer manufactured in Preparation Example 6. As shown in FIG. 9, it has been found that the substrate having the plasma polymerized TTMSS thin film as a first plasma polymer layer shows excellent inhibitory effect on cell adsorption.

This result suggests that the siloxne-based compound having a siloxane functional group such as hexamethyldisiloxane and tetrakis(trimethylsilyloxy)silane can be effectively used as a first precursor material to inhibit cell adsorption to a substrate.

Preparation Example 7

Formation of First Plasma Polymer Layer on Substrate by Using Hexamethylcyclotrisiloxane The first plasma polymer film was fabricated by PECVD system using hexamethylcyclotrisiloxane as a first precursor material contained in a bubbler. The bubbler containing hexamethylcyclotrisiloxane was heated to 90° C., vaporizing the precursor solution. Using the helium (He) gas having ultra-high purity of 99.999% as a carrier gas, the vaporized precursor was sprayed on the Si substrate through a shower head of the reactor for plasma deposition. The deposition was performed at the reactor pressure of 6.6×10-1 Torr, and at room temperature. The plasma power supplied by the radio frequency (RF) generator was changed from 10 to 50 W, and the plasma frequency was 13.56 MHz.

Experimental Example 4

In order to examine whether the substrate having a first plasma polymer layer manufactured in Preparation Example 7 is able to inhibit cell adsorption, NIH 3T3 mouse embryo fibroblast cells were cultured thereon. A culture medium was prepared by adding FBS (Fetal Bovine Serum) into DMEM (Dulbecco's modified Eagle's medium) including 4500 mg/l of high glucose to be a concentration of 20%, and supplemented with penicillin/streptomycin and insulin. The external condition while the cells were cultured on the substrate was 37° C., 5% CO2 environment (in a cell incubator).

It has been found that the substrate having the plasma polymerized hexamethylcyclotrisiloxane thin film as a first plasma polymer layer shows excellent inhibitory effect on cell adsorption.

Preparation Example 8

Formation of Second Patterned Plasma Polymer Layer on First Plasma Polymer Layer Ethylenediamine was used as a second precursor material having a functional group. A plasma polymerized ethylenediamine (PPEDA) thin film prepared by the inductively coupled plasma enhanced chemical vapor deposition was deposited by patterning using a shadow mask with a predetermined pattern on a glass slide having a size of 75 mm×25 mm (Corning Microslide Plain, Cat#: 2947, Corning, N.Y.), on which the plasma polymerized hexamethyldisiloxane thin film was deposited.

Specifically, the deposition was performed using an inductively coupled plasma enhanced chemical vapor deposition apparatus depicted in FIG. 2. The plasma reaction chamber 110 has a cylindrical shape of stainless material. The ethylenediamine precursor was placed into the bubbler 114 which was heated at 50° C. Ethylenediamine molecule was vaporized by using an inert gas of argon as a carrier gas and injected into the plasma reaction chamber 110. The inductively coupled plasma was generated around a shower ring 118 through an rf generator 116 where circular coil was coupled. SB power was supplied to attach the rf generator to a slide substrate holder to generate plasma around the slide. Here, the wall surface of the plasma reaction chamber 110 was put to earth. The substrate used upon deposition of plasma polymerized ethylenediamine thin film was the substrate having the first plasma polymer layer manufactured in Preparation Example 1.

As shown in (a) of FIG. 4, a shadow mask having a predetermined pattern was placed on the substrate having the first plasma polymer layer manufactured in Preparation Example 1. Here, the predetermined pattern of the shadow mask was provided with a plurality of holes having a diameter of 200 μm, and a space between the holes was 200 μm. Subsequently, ethylenediamine was deposited on the exposed region. The pressure of the plasma reaction chamber 110 was adjusted to about 10-5 torr by using the vacuum pump 112. During the deposition, the temperature of the substrate was maintained at room temperature and a flow rate of argon was maintained at 15 sccm. At this time, the deposition pressure of the plasma reaction chamber 110 was maintained at 30 mtorr, and the external electrode (ICP) and internal electrode (SB) of the plasma reaction chamber 110 was maintained at 3 W and 3 W, respectively. The deposition was performed for 2 min. In this manner, a patterned substrate for culturing cells, in which the second plasma polymer layer was patterned and deposited on the first plasma polymer layer, was manufactured.

Experimental Example 5

Rat intestinal epithelial cell was used to perform the experiment in order to examine the selective cell culturing ability of the patterned substrate for culturing cells, which was manufactured in Preparation Example 8.

Rat intestinal epithelial cell was cultured on the patterned substrate for culturing cells, which was manufactured in Preparation Example 8, and the time-dependent, selective cell culture degree was examined. At this time, the experiment was performed in the same manner as in Experimental Example 1, except that the patterned substrate for culturing cells manufactured in Preparation Example 8 was used and the culture degree was measured according to time.

FIG. 7 shows photographs of rat intestinal epithelial cells, which were cultured for 2 hrs, 8 hrs, and 24 hrs on the patterned substrate for culturing cells manufactured in Preparation Example 8, and the selective cell adsorption could be examined according to time. It was found that the inhibitory effect on cell adsorption was observed in the plasma polymerized hexamethyldisiloxane thin film-deposited region, and the cell culture was observed in the plasma polymerized ethylenediamine thin film-deposited region. Meanwhile, the cells cultured in the PPEDA-deposited region were found to grow normally as time passes.

Preparation Example 9

Formation of Second Patterned Plasma Polymer Layer on First Plasma Polymer Layer According to the same method as described in Preparation Example 8, a plasma polymerized EDA thin film prepared by the inductively coupled plasma enhanced chemical vapor deposition was deposited by patterning using a shadow mask with a predetermined pattern on each of the glass slides, on which the plasma polymerized TTMSS thin film prepared in Preparation Example 6 and the plasma polymerized hexamethylcyclotrisiloxane thin layer prepared in Preparation Example 7 were deposited, respectively.

Here, the predetermined pattern of the shadow mask was provided with a plurality of holes having a diameter of 200 μm, and a space between the holes was 200 μm. Subsequently, ethylenediamine was deposited on the exposed region. The pressure of the plasma reaction chamber 110 was adjusted to about 10-5 torr by using the vacuum pump 112. During the deposition, the temperature of the substrate was maintained at room temperature and a flow rate of argon was maintained at 15 sccm. At this time, the deposition pressure of the plasma reaction chamber 110 was maintained at 30 mtorr, and the external electrode (ICP) and internal electrode (SB) of the plasma reaction chamber 110 was maintained at 3 W and 3 W, respectively. The deposition was performed for 2 min. In this manner, a patterned substrate for culturing cells, in which the second plasma polymer layer (ethylenediamine) was patterned and deposited on the first plasma polymer layer (TTMS or hexamethylcyclotrisiloxane), was manufactured.

Experimental Example 6

Rat intestinal epithelial cell was used to perform the experiment in order to examine the selective cell culturing ability of the patterned substrate for culturing cells, which was manufactured in Preparation Example 9.

Rat intestinal epithelial cell was cultured on each of the patterned substrates for culturing cells, in which the plasma polymerized EDA thin film was patterned and deposited on the plasma polymerized TTMSS thin film or the plasma polymerized hexamethylcyclotrisiloxane thin film, and the time-dependent, selective cell culture degree was examined. At this time, the experiment was performed in the same manner as in Experimental Example 1, except that the patterned substrate for culturing cells manufactured in Preparation Example 9 was used and the culture degree was measured according to time.

As a result, it was found that the inhibitory effect on cell adsorption was observed in the plasma polymerized TTMSS or hexamethylcyclotrisiloxane thin film-deposited region, and the cell culture was observed in the plasma polymerized EDA thin film-deposited region. Meanwhile, the cells cultured in the plasma polymerized EDA-deposited region were found to grow normally as time passes.

While the present invention has been described with reference to particular embodiments, it is to be appreciated that various changes and modifications may be made by those skilled in the art without departing from the spirit and scope of the present invention, as defined by the appended claims and their equivalents.

The invention claimed is:

1. A method of manufacturing a patterned substrate for culturing cells, comprising the steps of:
   (1) preparing a substrate;
   (2) forming a first plasma polymer layer by integrating a first precursor material on the substrate using a plasma, wherein the first plasma layer inhibits cell adsorption and the first precursor material is a siloxane-based compound having a siloxane functional group with the Si—O—Si linkage;
   (3) placing a shadow mask having a predetermined pattern on the first plasma polymer layer thus formed; and
   (4) forming a second patterned plasma polymer layer by integrating a second precursor material using a plasma, wherein the second patterned plasma layer permits culturing of cells;
   whereby the patterned substrate is obtained.

2. The method according to claim 1, further comprising the step of forming the first patterned plasma polymer layer by integrating the first precursor material using a plasma between steps (3) and (4).

3. The method according to claim 1, wherein the substrate is selected from the group consisting of glass, plastic, metal and silicone.

4. The method according to claim 1, wherein the first precursor material is selected from the group consisting of styrene and n-hexane.

5. The method according to claim 1, wherein the siloxane-based compound is a linear siloxane compound or a cyclic siloxane compound.

6. The method according to claim 5, wherein the linear siloxane compound includes hexamethyldisiloxane, octamethyltrisiloxane, decamethyltetrasiloxane, dodecamethylpentasiloxane, and tetradecamethylhexasiloxane.

7. The method according to claim 5, wherein the cyclic siloxane compound includes hexamethylcyclotrisiloxane, octamethylcyclotetrasiloxane, decamethylcyclopentasiloxane, and dodecamethylcyclohexasiloxane.

8. The method according to claim 1, wherein the first precursor material is a siloxane-based compound represented by the following Formula 1:

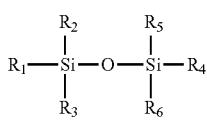

[Formula 1]

wherein R1, R2, and R3 are independently hydrogen or C1-C4 alkyl, and R4, R5, and R6 are independently hydrogen, C1-C4 alkyl or trialkylsilyloxy.

9. The method according to claim 8, wherein the first precursor material is a siloxane-based compound represented by one of the following Formulae 2 to 4:

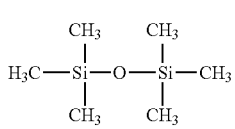

[Formula 2]

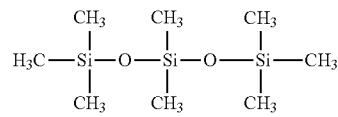

[Formula 3]

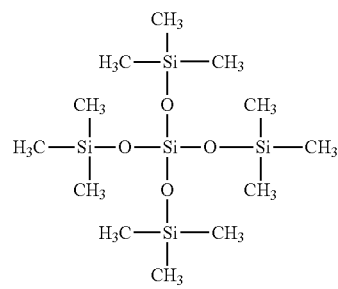

[Formula 4]

10. The method according to claim 1, wherein the first precursor material is a siloxane-based compound represented by the following Formula 5:

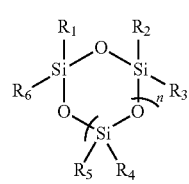

[Formula 5]

wherein R1, R2, R3, R4, R5, and R6 are independently hydrogen or C1-C4 alkyl, and n is an integer ranging from 1 to 3.

11. The method according to claim 1, wherein the second precursor material is selected from the group consisting of ethylenediamine, acetonitrile, allylamine, propylamine, cycloheptane, cyclohexane, and cyclopentane.

12. The method according to claim 1, wherein the first plasma polymer layer is formed by plasma enhanced chemical vapor deposition in step (2), and the second plasma polymer layer is formed by inductively coupled plasma enhanced chemical vapor deposition in step (4).

13. The method according to claim 1, wherein the first precursor material and the second precursor material are vaporized at the temperature of 30° C. to 70° C., and plasma-deposited.

14. The method according to claim 1, wherein the predetermined pattern of the shadow mask is provided with a plurality of holes having a diameter of 200 μm, and a space between the holes is 200 μm.

15. A patterning method for culturing cells, comprising the steps of:
   preparing a substrate for culturing cells which is patterned by the method according to claim 1; and
   culturing cells on the patterned substrate for culturing cells.

16. The method according to claim 15, wherein the cell is selected from the group consisting of microorganisms, cells and organs of animal/plant, neural cells, and endothelial cells.

* * * * *